United States Patent [19]

Alig et al.

[11] 4,361,578

[45] Nov. 30, 1982

[54] D-HOMOSTEROIDS

[76] Inventors: Leo Alig, 32 Liebrütistrasse, Kaiseraugst; Andor Fürst, 14 Magnolienpark, Basel; Peter Keller, 53 Hinterlindenweg, Reinach; Marcel Müller, 10 Quellenweg, Frenkendorf, all of Switzerland; Ulrich Kerb, 7 Prinzregentenstrasse; Rudolf Wiechert, 8a Petzower Strasse, both of Berlin, Fed. Rep. of Germany

[21] Appl. No.: 321,954

[22] Filed: Nov. 16, 1981

[30] Foreign Application Priority Data

Nov. 21, 1980 [CH] Switzerland .......................... 8622/80

[51] Int. Cl.³ ..................... A61K 31/34; C07D 307/94

[52] U.S. Cl. .................................... 424/285; 568/372; 260/464; 424/304; 424/305; 424/317; 424/320; 424/331; 549/331; 560/6; 562/403; 564/188

[58] Field of Search ........................... 260/464; 560/6; 562/403; 564/188; 568/372; 424/285, 304, 305, 317, 320, 331; 549/331

[56] References Cited

U.S. PATENT DOCUMENTS 2,874,179  2/1959  Hoehn ................................. 560/6 X
4,202,841  5/1980  Alig et al. ...................... 568/372 X Primary Examiner—Richard Raymond
Attorney, Agent, or Firm—Jon S. Saxe; Bernard S. Leon; James H. Callwood

[57] ABSTRACT

The invention is directed to 3-oxo-D-homosteroids and derivatives thereof which are useful as antiantigens.

34 Claims, No Drawings

D-HOMOSTEROIDS

SUMMARY OF THE INVENTION

The invention is directed to D-homosteroids of the formula

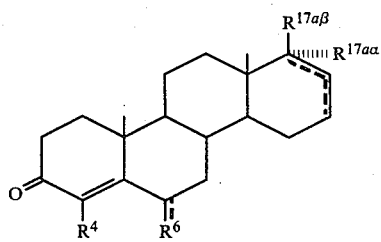

wherein $R^4$ is hydrogen, methyl, chlorine or hydroxy; $R^6$ is hydrogen or methylene; $R^{17a\alpha}$ is hydrogen, methyl or chlorine and $R^{17a\beta}$ is carboxy, esterified carboxy, cyano, formyl, carbamoyl, mono(lower alkyl)carbamoyl or di(lower alkyl)carbamoyl; or $R^{17a\alpha}$ and $R^{17a\beta}$ together are a spiroether ring of the formula

and wherein the dotted bonds in the D-ring are an optional 16(17)- or 17(17a)-double bond, whereby in the latter case $R^{17a\alpha}$ is absent.

The invention is also directed to a process for the preparation of the D-homosteroids of formula I as well as pharmaceutical preparations containing said D-homosteroids.

DETAILED DESCRIPTION OF THE INVENTION

The term "esterified carboxy" refers to carboxyl groups which are esterified with an aliphatic, cycloaliphatic, aromatic or araliphatic group. Examples of esterified carboxy groups are alkoxycarbonyl, especially lower alkoxycarbonyl, optionally substituted by halogen (for example, chlorine) or amino, such as methoxycarbonyl, ethoxycarbonyl, propoxycarbonyl and butoxycarbonyl, cycloalkoxycarbonyl such as cyclohexyloxycarbonyl and cyclopentyloxycarbonyl, aryloxycarbonyl, such as phenyloxycarbonyl and tolyloxycarbonyl, and aralkoxycarbonyl such as benzyloxycarbonyl. Examples of mono(lower alkyl) [for example, alkyl groups containing 1-7 carbon atoms] carbamoyl groups are methylcarbamoyl, ethylcarbamoyl and propylcarbamoyl and lower alkylamino-substituted lower alkylcarbamoyl such as di(lower alkyl)amino-ethylcarbamoyl. Examples of di(lower alkyl)carbamoyl groups are dimethylcarbamoyl, diethylcarbamoyl, dipropylcarbamoyl and N-methyl-N-ethyl-carbamoyl.

Preferred D-homosteroids of formula I are those in which $R^4$, $R^6$ and $R^{17a\alpha}$ are hydrogen and $R^{17a\beta}$ is carboxy, lower alkoxycarbonyl or cyano, or $R^{17a\alpha}$ and $R^{17a\beta}$ together are a spiroether ring as defined earlier. Especially preferred among these D-homosteroids are those in which $R^{17a\beta}$ is carboxy or lower alkoxycarbonyl and the D-ring is saturated such as 3-oxo-D-homo-androst-4-ene-17aβ-carboxylic acid and its methyl ester.

The D-homosteroids of formula I can be prepared in accordance with the invention by (a) treating a D-homosteroid of the formula

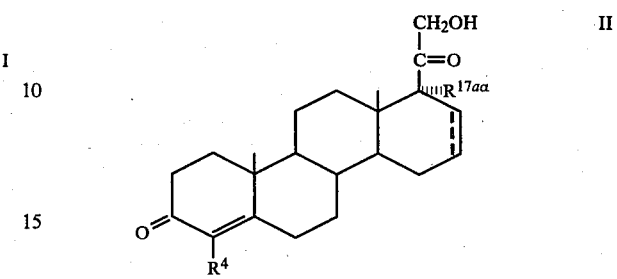

with an oxidizing agent; or (b) treating a D-homosteroid of the formula

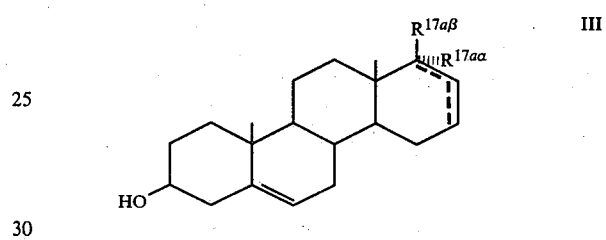

with an oxidizing agent; or (c) dehydrating a D-homosteroid of the formula

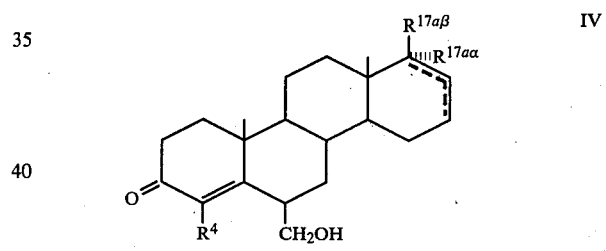

or (d) cyclizing a D-homosteroid of the formula

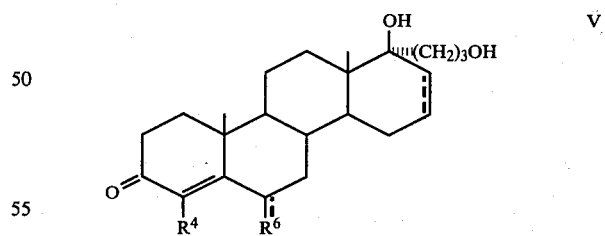

to the ether; or (e) esterifying the carboxy group in a D-homosteroid of formula I in which $R^{17a\beta}$ is carboxy; or (f) saponifying the esterified carboxy group in a D-homosteroid of formula I in which $R^{17a\beta}$ is esterified carboxy; or (g) methylating, chlorinating or hydroxylating in the 4-position a D-homosteroid of formula I in which $R^4$ and $R^6$ are hydrogen; or (h) amidating the carboxy group in a D-homosteroid of formula I in which $R^{17a\beta}$ is carboxy; or (i) transforming the carbamoyl group in a D-homosteroid of formula I in which $R^{17a\beta}$ is carbamoyl into the cyano group;

in formulas II, III, IV and V, $R^4$, $R^6$, $R^{17a\alpha}$, $R^{17a\beta}$ and the dotted bonds in the D-ring have the significance given earlier.

The oxidation of a D-homosteroid of formula II in accordance with process variant (a) yields a D-homosteroid of formula I in which $R^{17a\beta}$ is carboxy. Reagents such as periodic acid can be used as the oxidizing agent. The oxidation is conveniently carried out at room temperature. Suitable solvents are those in which both reaction partners are soluble (for example, aqueous alcohols).

The oxidation of the 3-hydroxy-$\Delta^5$-grouping of a D-homosteroid of formula III to the corresponding 3-keto-$\Delta^4$-D-homosteroids in accordance with process variant (b) can be carried out by means of the Oppenauer reaction (for example, using aluminium isopropylate) or using oxidizing agents such as chromium trioxide (for example, Jones' reagent) or according to Pfitzner-Moffatt using dimethyl sulphoxide/dicyclohexylcarbodiimide (the primarily-obtained $\Delta^5$-3-ketone requiring subsequent isomerization to the $\Delta^4$-3-ketone) or using pyridine/sulphur trioxide.

The dehydration of the hydroxymethyl group of a D-homosteroid of formula IV in accordance with process variant (c) to give a D-homosteroid of formula I in which $R^6$ is methylene can be carried out by treatment with acids such as p-toluenesulphonic acid.

The cyclization in accordance with process variant (d) to give D-homosteroids of formula I in which $R^{17a\alpha}$ and $R^{17a\beta}$ together form a spiroether group of the formula

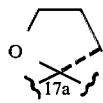

can be carried out by treatment with a dehydrating agent, for example, p-toluenesulphonyl chloride or methanesulphonyl chloride in pyridine.

The esterification of a 17a$\beta$-carboxy group in a D-homosteroid of formula I in accordance with process variant (e) can be carried out, for example, by treating the acid with a diazoalkane such as diazomethane in ether or with an O-alkyl-N,N'-dicyclohexylisourea in an aprotic solvent (for example, dimethylacetamide or dimethylformamide) or by reacting a salt of the acid (for example, an alkali salt) with an alkyl, cycloalkyl, aryl or aralkyl halide.

An esterified carboxy group denoted by $R^{17a\beta}$ can be saponified to the carboxy group in accordance with process variant (f) by treatment with alkaline reagents such as alcoholic alkali hydroxides, for example, methanolic potassium hydroxide at elevated temperature.

The chlorination in accordance with process variant (g) is conveniently carried out by introducing chlorine or sulphuryl chloride into a medium which contains the steroid starting material of formula I. The chlorination can be carried out in the presence of a proton acceptor, for example, pyridine, picoline, dimethylformamide or dimethylazetamide; or ethylene oxide or propylene oxide, optionally with the addition of a further solvent such as benzene. Alternatively, the chlorination can be carried out in the absence of a proton acceptor. In this case, the initial chlorination product is subsequently treated with one of the aforementioned proton acceptors.

A preferred method for the introduction of a 4-hydroxy group comprises reacting a 4,5-saturated steroid starting material with a strong base such as potassium tert.butylate in tert.butanol while aerating (oxygen introduction) (see Tetrahedron Lett. 1961, 554). 4-hydroxy-D-homosteroids of formula I can also be obtained by the alkaline hydrolysis of corresponding 4-halo-D-homosteroids [see II Farmaco-Ed. Pr. 17, 721 (1962)].

The 4-methylation in accordance with process variant (g) can be carried out, for example, by converting a 4-unsubstituted D-homosteroid of formula I by reaction with pyrrolidine or another secondary cyclic amine (for example, morpholine or piperidine) into a 3-enamine, reacting this enamine with a methylating agent (for example, a methyl halide) and cleaving off the enamine group from the product by hydrolysis.

The methylation of the 3-enamine is preferably carried out in the presence of an organic solvent such as ethanol, methanol or ethyl acetate, but especially dimethylformamide, etc. The iodide or bromide is conveniently used as the halide. The hydrolysis of the 3-enamine group in order to reintroduce the original 3-keto-$\Delta^4$-grouping can be carried out in a manner known in the art; for example, with water, aqueous acid or base (for example, with a solution of sodium hydroxide in aqueous methanol) or takes place directly in the course of the alkylation or aralkylation such as, for example, when dimethylformamide is used as the solvent. A further method for the 4-methylation comprises converting the 3-keto-$\Delta^4$-steroid starting material with formaldehyde and a thiol (for example, an aliphatic, aromatic, alicyclic or heterocyclic thiol such as ethyl metcaptan, thiophenol, cyclohexyl mercaptan or pyridyl metcaptan) in the presence of a base, especially an organic base such as a tertiary amine (for example, trialkylamine) into a thiomethyl ether, for example, the phenylthiomethyl ether, and reductively desulphurizing the latter to the $\Delta^4$-4-methyl compound, for example, with deactivated Raney-nickel (see, for example, Chem. Soc. 1962, 1091).

Furthermore, a 3-keto-$\Delta^4$-steroid starting material can be methylated in the 4-position with a methylating agent, especially a methyl iodide or bromide in the presence of a proton acceptor such as potassium tert.butylate in tert.butanol [see, for example, J. Am. Chem. Soc. 85, 196 (1963)].

The transformation of a carboxyl group denoted by $R^{17a\beta}$ into a carbamoyl group in accordance with process variant (h) can be carried out by converting the carboxylic acid into an acid halide (for example, using an acyl halide such as oxalyl chloride) and reacting the acid halide with ammonia or a mono(lower alkyl)amine or di(lower alkyl)amine.

The dehydration of an acid amide, i.e., a D-homosteroid of formula I in which $R^{17a\beta}$ is carbamoyl, to give a D-homosteroid of formula I in which $R^{17a\beta}$ is cyano, can be carried out using mild dehydrating agents such as triphenylphosphine oxide/trifluoroacetic anhydride.

The D-homosteroids of formulas II–V used as the starting materials are known or can be prepared as described in the following examples or in analogy thereto.

The D-homosteroids of formula I are therapeutically active. In particular, they are active as 5α-reductase inhibitors and can accordingly be used as antiandrogens, for example, for the treatment of acne, hirsutism and prostate hypertrophy. The D-homosteroids of formula I can be administered topically (for example, in the case of acne), enterally or parenterally.

The activity of the D-homosteroids of formula I in the inhibition of 5α-reductase in vitro was determined according to a modified method of M. S. P. Manandhar and J. A. Thomas [Investigat. Urology 14 (1976) 20–22]. The enzyme preparation used was a 10% (weight-/volume) homogenate of ventral prostate glands of albino rats (weighing 180–200 g in ice-cold 0.05 M glycylglycine buffer (pH 7.0). The homogenate was filtered through nylon gauze and diluted to 1% with buffer solution before carrying out the test.

The substrate used was 6 picomoles of [1,2,6,7-$^3$H] testosterone (83 Ci/mMol) in 100 μl of benzene which was evaporated in a nitrogen stream. Thereto there were added 1.5 ml of a NADPH-yielding system consisting of $10^{-4}$ M NADP, 5 I.U. of glucose-6-phosphate dehydrogenase, $4 \times 10^{-3}$ M glucose-6-phosphate and $5 \times 10^{-5}$ M dithiothreit, and the mixture was preincubated for 10 minutes at 37° C. in a water-bath while shaking. The test compounds were added in solution in 20 μl of dimethyl sulphoxide, there being maintained a concentration range which amounted to 0.1 to 50-fold of the substrate concentration before the preincubation. Triple determinations were carried out on all concentrations. The reaction was initiated by adding 0.5 ml of homogenate, and the incubation was terminated after 6 minutes by adding 5 ml of dichloromethane. After extraction with 15 ml of dichloromethane and addition of nonlabelled 3α-androstanediol, 5α-androstanedione, androstenedione, epi-androsterone, testosterone and 5α-dihydrotestosterone (20 μg of each), the extracts were evaporated to dryness, and the residue was dissolved in a minimum of methanol and subjected to a thin-layer chromatography on Silica gel 60 (E. Merck) with benzene/acetone (85:15) as the solvent. The separated steroids were developed by spraying with a mixture of concentrated sulphuric acid and ethanol (1:1) and heating at 100° C. for 10 minutes. The corresponding spots were cut out, placed in counting test tubes and measured in a scintillation counter.

The in vivo testing was carried out as follows:

Adult male albino rats weighing 200 g were castrated. Two hours later they received the first of 10 daily dosages of the test substance suspended in 0.5% carboxymethylcellulose, 0.4% Tween 80 and 0.9% benzyl alcohol in physiological sodium chloride solution. Three hours after the last medication on the tenth day of treatment, the animals were decapitated, the blood from the body was collected, and the seminal vesicles, the ventral prostate and the Levator ani muscle were removed and weighed. The results are given as ng of NIAMDD-RP-1/ml.

Test substances:

A. 3-oxo-D-homo-androst-4-ene-17aα-carboxylic acid.
B. 2-diethylamino-ethyl 3-oxo-D-homo-androsta-4,17-diene-17a-carboxylate.
C. methyl 17a-methyl-3-oxo-D-homo-androsta-4,16-diene-17aβ-carboxylate.
D. methyl 4-chloro-3-oxo-D-homo-androst-4-ene-17aβ-carboxylate.
E. methyl 3-oxo-D-homo-androsta-4,17-diene-17a-carboxamide.
F. 4,5-dihydrospiro[furan-2(3H),17'a(β1)-D-homo-androsta-4,16-dien]-3'-one.
G. methyl 3-oxo-D-homo-androst-4-ene-17aβ-carboxylate.
H. chloromethyl 3-oxo-D-homo-androsta-4,17-diene-17a-carboxylate.
I. methyl 3-oxo-4-methyl-D-homo-androst-4-ene-17aβ-carboxylate.
J. 3-oxo-D-homo-androst-4-ene-17aβ-carboxamide.
K. 4,5-dihydro-6'-methylenespiro[furan-2(3H),17'a(β1)-D-homo-androsta-4,16-dien]-3'-one.
L. methyl 3-oxo-D-homo-androsta-4,17-diene-17a-carboxylate.
M. dimethyl 3-oxo-D-homo-androst-4-ene-17aβ-carboxamide.
N. 3-oxo-D-homo-androst-4-ene-17aβ-carbonitrile.

Results:
(a) Inhibition of 5α-reductase in vitro

| Test substance | IC$_{50}$ |
|---|---|
| A | 1:4 |
| B | 1:2 |
| C | 1:6 |
| D | 1:2 |
| E | 1:5 |
| F | 1:6 |
| G | 1:0.3 |
| H | 1:4 |
| I | 1:16 |
| J | 1:7 |
| K | 1:1 |
| L | 1:2 |
| M | 1:4 |
| N | 1:0.8 |

IC$_{50}$ denotes the molar ratio of testosterone to test substance at which the transformation of the testosterone into dihydrotestosterone is reduced to half.

| (b) Inhibition of 5α-reductase in vivo | | | | | | |
|---|---|---|---|---|---|---|
| Test substance | Dosage (mg/kg) | VP (mg) | SV (mg) | MLA (mg) | LH (ng/ml) | FSH (ng/ml) |
| Control sc | — | 20 ± 1 | 50 ± 3 | 61 ± 3 | 325 ± 20 | 1040 ± 51 |
| Testosterone propionate(TP) | 0.5 | 160 ± 18 | 215 ± 13 | 137 ± 7 | 101 ± 36 | 783 ± 167 |
| A sc | 15 | | | | | |
| + TP sc | + 0.5 | 116 ± 11 | 157 ± 15 | 118 ± 8 | 283 ± 41 | 1268 ± 125 |
| Control sc | — | 48 ± 4 | 38 ± 6 | 60 ± 10 | 271 ± 18 | 1055 ± 35 |
| TP sc | 0.5 | 108 ± 6 | 69 ± 3 | 75 ± 4 | 121 ± 12 | 915 ± 37 |
| L sc | 15 | | | | | |
| + TP sc | + 0.5 | 80 ± 6 | 52 ± 1 | 67 ± 6 | 163 ± 30 | 1099 ± 94 |
| Control sc | — | 16 ± 1 | 20 ± 1 | 52 ± 2 | 402 ± 18 | 1289 ± 50 |
| Testosterone sc (T) | 0.5 | 112 ± 10 | 65 ± 5 | 108 ± 5 | 104 ± 25 | 1206 ± 114 |
| D sc | 10 | | | | | |

-continued

(b) Inhibition of 5α-reductase in vivo

| Test substance | Dosage (mg/kg) | VP (mg) | SV (mg) | MLA (mg) | LH (ng/ml) | FSH (ng/ml) |
|---|---|---|---|---|---|---|
| + T sc | + 0.5 | 95 ± 10 | 51 ± 9 | 83 ± 6 | 244 ± 45 | 1325 ± 93 |
| Control po | — | 16 ± 1 | 24 ± 2 | 47 ± 4 | — | — |
| T sc | 0.5 | 96 ± 10 | 92 ± 13 | 109 ± 8 | — | — |
| L po | 30 | | | | | |
| + T sc | + 0.5 | 81 ± 16 | 68 ± 13 | 88 ± 17 | — | — |
| Control sc | — | 16 ± 1 | 18 ± 2 | 51 ± 2 | 283 ± 27 | — |
| T sc | 0.5 | 128 ± 12 | 85 ± 7 | 126 ± 7 | 96 ± 37 | — |
| F sc | 10 | | | | | |
| + T sc | + 0.5 | 93 ± 10 | 66 ± 4 | 105 ± 6 | 88 ± 15 | — |

VP: Ventral prostrate, SV: Seminal vesicle, MLA: Levator ani muscle
LH: Luteinizing hormone, FSH: Follicle stimulating hormone The D-homosteroids of formula I can be used as medicaments, for example, in the form of pharmaceutical preparations which contain them or their salts in association with a pharmaceutical, organic or inorganic inert carrier material suitable for enteral, percutaneous or parenteral administration such as, for example, water, gelatine, gum arabic, lactose, starch, magnesium sulphate, talc, vegetable oils, polyalkyleneglycols, petroleum jelly, etc. The pharmaceutical preparations can be made up in a solid form (for example, as tablets, dragees, suppositories or capsules), in a semisolid form (for example, as ointments) or in a liquid form (for example, as solutions, suspensions or emulsions). The pharmaceutical preparations may be sterilized and/or may contain adjuvants such as preserving, stabilizing, wetting or emulsifying agents, salts for varying the osmotic pressure or buffers. They can also contain still other therapeutically valuable substances.

The following examples illustrate the present invention:

EXAMPLE 1

10.0 g of 21-hydroxy-D-homo-pregn-4-ene-3,20-dione were dissolved in 500 ml of methanol and treated with a solution of 15.0 g of periodic acid in 100 ml of water. The solution was held at room temperature for 2½ hours. For the working-up, the solution was poured into 3 l of water, the separated precipitate was filtered off under suction and dried at 60° in vacuo over potassium hydroxide. The residue was recrystallized from methylene chloride/isopropyl ether. The pure 3-oxo-D-homo-androst-4-ene-17aβ-carboxylic acid melted at 238°–240° $[\alpha]_D^{25} = +98°$ (c=0.1 in dioxane).

EXAMPLE 2

A mixture of 3.8 g of 3-oxo-D-homo-androst-4-ene-17aβ-carboxylic acid, 1.90 ml of methyl iodide, 1.90 g of sodium hydrogen carbonate and 20 ml of N,N-dimethylacetamide was stirred at room temperature for 24 hours. For the working-up, the mixture was poured into ice water, extracted with ether, the ether extract was dried with sodium sulphate and evaporated in vacuo. The residue was chromatographed on a 50-fold amount of silica gel with methylene chloride/acetone (99:1). The thin-layer chromatographically uniform fractions were recrystallized from ether/hexane and yielded pure methyl 3-oxo-D-homo-androst-3-ene-17aβ-carboxylate, m.p. 132°–134°, $[\alpha]_D^{25} = +147°$ (c=0.1 in dioxane).

In a manner analogous to that described in this example, from 3-oxo-D-homo-androsta-4,17-diene-17a-carboxylic acid and isopropyl iodide there was obtained isopropyl 3-oxo-D-homo-androsta-4,17-diene-17a-carboxylate, m.p. 83°–84°, $[\alpha]_D^{25} = +180°$ (c=1.0 in dioxane);

from 3-oxo-D-homo-androsta-4,17-diene-17a-carboxylic acid and 2-diethylamino-ethanol there was obtained 2-diethylamino-ethyl 3-oxo-D-homo-androsta-4,17-diene-17a-carboxylate, m.p. 75°–77° (acetone/hexane), $[\alpha]_D^{20} = 158°$ (c=1.0 in dioxane);

from 3-oxo-D-homo-androsta-4,17-diene-17a-carboxylic acid and chloroiodomethane there was obtained chloromethyl 3-oxo-D-homo-androsta-5,17-diene-17a-carboxylate, m.p. 144°–145° (acetone/hexane), $[\alpha]_D^{20} = +179°$ (c=0.1 in dioxane).

EXAMPLE 3

A mixture of 13.8 g of methyl 3β-hydroxy-D-homo-androsta-5,17-diene-17aβ-carboxylate, 600 ml of absolute toluene, 270 ml of cyclohexanone and 16.6 g of aluminium tert.butylate was heated under reflux on a water-separator for 1½ hours. The mixture was cooled, poured into ice water and extracted with methylene chloride. The extract was washed with water, dried with sodium sulphate and evaporated in vacuo. The residue was chromatographed on 1 kg of silica gel. Pure methyl 3-oxo-D-homo-androsta-4,17-diene-17a-carboxylate of melting point 140°–141° was eluted with methylene chloride/acetone 98:2; $[\alpha]_D^{25} = +178°$ (c=0.1 in dioxane).

The starting material was prepared as follows:

3β-acetoxy-D-homo-androst-5-en-17a-one was reacted with dichloromethyl lithium at −60° and the intermediately-obtained "dichloroepoxide" was transformed by heating in toluene into 3β-acetoxy-17aα-chloro-D-homo-androst-5-ene-17a-carboxaldehyde of melting point 149°–151°. The aldehyde was oxidized with chromic acid to 3β-acetoxy-17aα-chloro-D-homo-androst-5-ene-17a-carboxylic acid. Treatment of the carboxylic acid with lithium carbonate/dimethylformamide at 60° yielded 3β-acetoxy-D-homo-androsta-5,17-diene-17a-carboxylic acid from which the methyl ester (m.p. 182°–183°) was obtained with methyl iodide in dimethylacetamide in the presence of sodium hydrogen carbonate. Saponification of the methyl ester with sodium methylate in methanol at room temperature yielded methyl 3β-hydroxy-D-homo-androsta-5,17-diene-17aβ-carboxylate, m.p. 197°–198°.

EXAMPLE 4

In a manner analogous to that described in Example 3,
from methyl 3β-hydroxy-17a-methyl-D-homo-androsta-5,16-diene-17aβ-carboxylate there was obtained methyl 17a-methyl-3-oxo-D-homo-androsta-4,16-diene-17aβ-carboxylate, m.p. 130°–132°, $[\alpha]_D^{25} = +22.6°$ (c=0.7 in dioxane).

The starting material was prepared by reacting methyl 3β-hydroxy-D-homo-androsta-5,17-diene-17aβ-carboxylate with methyl iodide in dimethylformamide in the presence of potassium tert.butylate at 50°.

EXAMPLE 5

In a manner analogous to that described in Example 3,
from methyl 3β-hydroxy-17a-methyl-D-homo-androst-5-ene-17aβ-carboxylate there was obtained methyl 17a-methyl-3-oxo-D-homo-androst-5-ene-17aβ-carboxylate, m.p. 123°–124°, $[\alpha]_D^{25} = +84°$ (c=1.0 in dioxane).

The starting material was obtained by catalytically hydrogenating methyl 3β-hydroxy-17a-methyl-D-homo-androsta-5,16-diene-17aβ-carboxylate.

EXAMPLE 6

In a manner analogous to that described in Example 3,
from 3β-hydroxy-D-homo-androsta-5,17-diene-17a-carboxaldehyde there was obtained 3-oxo-D-homo-androsta-4,17-diene-17a-carboxaldehyde, m.p. 145°–148°, $[\alpha]_D^{25} = +178°$ (c=0.1 in dioxane).

The starting material was obtained from 3β-acetoxy-17aα-chloro-D-homo-androst-5-ene-17a-carboxaldehyde by cleaving the chlorine with lithium carbonate in dimethyl-formamide and subsequently saponifying the 3-acetate with potassium carbonate in methanol.

EXAMPLE 7

A mixture of 4.0 g of methyl 3-oxo-D-homo-androsta-4,17-diene-17a-carboxylate, 10 g of lithium iodide and 300 ml of collidine was heated under reflux for 16 hours. For the working-up, the mixture was poured into ice water, adjusted to pH 11 with potassium hydroxide and extracted three times with ether. The aqueous-alkaline solution was acidified to pH 2 with hydrochloric acid and extracted three times with ether/methylene chloride (3:1). The ether/methylene chloride extract was washed with water, dried with sodium sulphate and evaporated in vacuo. The residue was crystallized from methanol, and there was obtained pure 3-oxo-D-homo-androsta-4,17-diene-17a-carboxylic acid, m.p. 229°–231°, $[\alpha]_D^{25} = +205°$ (c=0.1 in dioxane).

According to the same method, from methyl 4-methyl-3-oxo-D-homo-androsta-4,17-diene-17a-carboxylate there was obtained 4-methyl-3-oxo-D-homo-androsta-4,17-diene-17a-carboxylic acid [m.p. 280°–283°, $[\alpha]_D^{25} = +210°$ (c=0.5 in dioxane)] and from methyl 4-methyl-3-oxo-D-homo-androst-4-ene-17aβ-carboxylate there was obtained 4-methyl-3-oxo-D-homo-androst-4-ene-17aβ-carboxylic acid [m.p. 258°–259°, $[\alpha]_D^{25} = +129.7°$ (c=1.0 in dioxane)].

EXAMPLE 8

A mixture of 0.55 ml of methyl iodide and 100 ml of tert.butanol was added dropwise during 2½ hours to a well-stirred solution, boiling under reflux, of 2.0 g of methyl 3-oxo-D-homo-androst-4-ene-17aβ-carboxylate and 1.16 g of potassium tert.butylate in 40 ml of tert-.butanol. The mixture was then cooled, acidified with 20 ml of 2 N hydrochloric acid, concentrated in vacuo to a small volume, poured into water and extracted with ether. The ether extract was washed with water, dried with sodium sulphate and evaporated in vacuo. The residue was chromatographed on 150 g of silica gel. The pure fractions, eluted with hexane/ether (3:1), were recrystallized from acetone/hexane and yielded pure methyl 3-oxo-4-methyl-D-homo-androst-4-ene-17aβ-carboxylate, m.p. 130°–132°, $[\alpha]_D^{25} = 147°$ (c=1.0 in dioxane).

EXAMPLE 9

0.34 ml of sulphuryl chloride was added dropwise while stirring to a solution of 0.684 g of methyl 3-oxo-D-homo-androsta-4,17-diene-17a-carboxylate in 10 ml of pyridine. The solution was held at room temperature for 15 minutes and then poured into ice water and extracted with methylene chloride. The extract was washed neutral with dilute hydrochloric acid and water, dried with sodium sulphate and evaporated in vacuo. The residue was chromatographed on 30 g of silica gel. Pure methyl 4-chloro-3-oxo-D-homo-androsta-4,17-diene-17a-carboxylate could be eluted with hexane/ether. m.p. 148°–152° (acetone/hexane), $[\alpha]_D^{25} = +11.8°$ (c=1.0 in dioxane).

In an analogous manner,
from methyl 3-oxo-D-homo-androst-4-ene-17aβ-carboxylate there was obtained methyl 4-chloro-3-oxo-D-homo-androst-4-ene-17aβ-carboxylate, m.p. 163°–164°, $[\alpha]_D^{25} = +154.8°$ (c=0.8 in dioxane).

EXAMPLE 10

A mixture of 2.0 g of methyl 3-oxo-D-homo-androsta-4,17-diene-17a-carboxylate, 1.6 g of thiophenol, 2.0 g of 40% formaldehyde solution and 4.0 g of triethanolamine was heated under reflux for 18 hours. Then, the mixture was poured into ice water, extracted with methylene chloride, the extract was washed neutral with dilute hydrochloric acid, dilute sodium hydroxide and water, dried with sodium sulphate and evaporated in vacuo. There was obtained 2.7 g of crude 4-phenylthiomethyl compound which was heated under reflux for 40 hours in 70 ml of acetone with 10 g of deactivated Raney-nickel. The cooled mixture was filtered, and the filtrate was evaporated in vacuo. The residue was chromatographed on 150 g of silica gel. 0.9 g of pure methyl 4-methyl-3-oxo-D-homo-androsta-4,17-diene-17a-carboxylate could be eluted with methylene chloride. m.p. 121°–122°, $[\alpha]_D^{25} = +212°$ (c=0.29 in dioxane).

EXAMPLE 11

289 mg of methyl 17a-chloro-3β-hydroxy-D-homoandrost-5-ene-17aβ-carboxylate was treated at 0° under argon in 23 ml of acetone with 0.285 ml of Jones' reagent. After 5 minutes, the mixture was washed with 1 ml of isopropanol, and, after a further 5 minutes, the mixture was diluted with water and methylene chloride. The organic phase was washed neutral with water, dried and evaporated in vacuo. The residue obtained was stirred at 20° for 1 hour in 8 ml of glacial acetic acid and 0.8 ml of 2 N hydrochloric acid. The mixture was evaporated to dryness. Chromatography of the residue on silica gel gave methyl 17a-chloro-3-oxo-D-homo-androst-4-ene-17aβ-carboxylate, m.p. 163°, $[\alpha]_D^{25} = +53°$ (c=0.1 in dioxane).

EXAMPLE 12

A mixture of 0.68 g of methyl 3-oxo-D-homo-androsta-4,17-diene-17a-carboxylate, 15 ml of methanol, 0.7 ml of 10% sodium hydroxide and 1.4 ml of 30% hydrogen peroxide was held at 0° for 23 hours. For the working-up, the mixture was treated with 0.2 ml of acetic acid, poured into ice water and extracted with methylene chloride. The extract was evaporated in vacuo, dissolved in 30 ml of methanol and treated with 6 ml of water and 6 ml of 2 N sulphuric acid. The mixture was held at room temperature for 40 hours and then poured into ice water and extracted with methylene chloride. The extract was washed with water, dried with sodium sulphate, evaporated in vacuo, and the residue was chromatographed on silica gel. Pure methyl 4-hydroxy-3-oxo-D-homo-androsta-4,17-diene-17a-carboxylate could be eluted with methylene chloride. m.p. 176°–179°, $[\alpha]_D^{25} = +192.6°$ (c=0.5 in dioxane).

In an analogous manner, from methyl 3-oxo-D-homo-androst-4-ene-17aβ-carboxylate there was obtained methyl 4-hydroxy-3-oxo-D-homoandrost-4-ene-17aβ-carboxylate, m.p. 184°–187°, $[\alpha]_D^{25} = +127°$ (c=0.73 in dioxane).

EXAMPLE 13

A mixture of 0.68 ml of Jones' reagent in 2 ml of acetone was added dropwise while stirring to a solution, cooled to 0°, of 0.713 g of 3β-hydroxy-D-homo-androst-5-ene-17β-carboxaldehyde in 20 ml of acetone and 20 ml of methylene chloride. Subsequently, the mixture was stirred for a further 15 minutes, treated with 1 ml of isopropyl alcohol, poured into ice water and extracted with methylene chloride. Usual working-up yielded 650 mg of crude product which was dissolved in 20 ml of acetic acid and 2 ml of 2 N hydrochloric acid and held at room temperature for 2 hours. For the working-up, the mixture was poured into ice water, extracted with methylene chloride, the methylene chloride extract was washed with water, dried with sodium sulphate and evaporated in vacuo. The residue was chromatographed on silica gel. Pure 3-oxo-D-homo-androst-4-ene-17aβ-carboxaldehyde could be eluted with methylene chloride. m.p. 123°–125°, $[\alpha]_D^{25} = +133°$.

In an analogous manner, from 3β-hydroxy-17a-methyl-D-homo-androsta-5,16-diene-17aβ-carboxylic acid there was obtained 17a-methyl-3-oxo-D-homo-androsta-4,16-diene-17aβ-carboxylic acid, m.p. 270°–280°, $[\alpha]_D^{25} = 0°$ (c=0.2 in dioxane).

EXAMPLE 14

4.5 ml of oxalyl chloride was added dropwise while stirring to a suspension, cooled to 5°, of 0.99 g of 3-oxo-D-homo-androst-4-ene-17aβ-carboxylic acid in 30 ml of benzene. The solution was stirred at room temperature for 20 minutes and subsequently evaporated in vacuo. The residue was dissolved in 25 ml of benzene, and then ammonia was conducted into the solution for 30 minutes. The precipitated ammonium chloride was filtered off, and the filtrate was concentrated in vacuo. The residue was chromatographed on silica gel. Pure 3-oxo-D-homo-androst-4-ene-17aβ-carboxamide was eluted with methylene chloride/acetone (5:1). m.p. 226°–227° (acetone/hexane), $[\alpha]_D^{25} = +144°$ (c=0.4 in dioxane).

In an analogous manner, from 3-oxo-D-homo-androst-4-ene-17aβ-carboxylic acid and dimethylamine there was obtained dimethyl 3-oxo-D-homo-androst-4-ene-17aβ-carboxamide, m.p. 153°–154° (acetone/hexane); $[\alpha]_D^{25} = 115°$ (c=0.4 in dioxane);

from 3-oxo-D-homo-androsta-4,17-diene-17a-carboxylic acid and methylamine there was obtained methyl 3-oxo-D-homo-androsta-4,17-diene-17a-carboxamide, m.p. 256°–257° (acetone/hexane), $[\alpha]_D^{20} = +196°$ (c=0.4 in dioxane);

from 3-oxo-D-homo-androst-4-ene-17a-carboxylic acid and 2-diethylamino-ethylamine there was obtained 2-diethylamino-ethyl 3-oxo-D-homo-androst-4-ene-17aβ-carboxamide hydrochloride as an amorphous substance, $[\alpha]_D^{20} = +59°$ (c=0.15 in dioxane).

EXAMPLE 15

A solution of 1.2 ml of trifluoroacetic acid anhydride in 15 ml of methylene chloride was added at 0°–5° while stirring to a mixture of 2.1 g of triphenylphosphine oxide and 15 ml of methylene chloride. The mixture was stirred at 0°–5° for 15 minutes and then 1.4 g of 3-oxo-D-homo-androst-4-ene-17aβ-carboxamide in 10 ml of methylene chloride was added. The mixture was stirred at room temperature for 16 hours and then poured into ice water and extracted with methylene chloride. The organic extract was washed neutral with water, dried with sodium sulphate and evaporated in vacuo. The residue was chromatographed on silica gel. Pure 3-oxo-D-homo-androst-4-ene-17aβ-carbonitrile was eluted with hexane/acetone (95:5), m.p. 133°–135°, $[\alpha]_D^{20} = +137°$ (c=0.15 in dioxane).

EXAMPLE 16

28 g of p-toluenesulphonyl chloride was added to a solution of 44.6 g of 17aβ-hydroxy-17a-(3'-hydroxypropyl)-D-homo-androsta-4,16-diene-3-one in 200 ml of pyridine, and the mixture was stirred at room temperature for 3 hours. The mixture was poured into ice water, extracted with ether, the ether extract was washed with 1 N sodium hydroxide and subsequently with water, dried with sodium sulphate and evaporated in vacuo. The residue was chromatographed on 1.2 kg of silica gel. 30 g of pure 4,5-dihydrospiro[furan-2(3H),17'a(β1)-D-homoandrosta-4,16-dien]-3'-one could be isolated with toluene/ethyl acetate (95:5). m.p. 131°–132° (acetone/hexane), $[\alpha]_D^{25} = +8°$ (c=0.1 in methanol).

The starting material was prepared by reducing 3-oxo-D-homo-17aα-pregna-4,16-diene-21,17a-carbolactone with lithium aluminium hydride and oxidizing the resulting 3-ol with manganese dioxide.

EXAMPLE 17

5.65 g of 1-[4,5-dihydrospiro]furan-2(3H),17'a(β1)-D-homoandrosta[3,5,16]trien-3'-yl]pyrollidine was dissolved in 350 ml of benzene, 175 ml of methanol and 10 ml of 35% formaldehyde solution, and the mixture was stirred at room temperature for 45 minutes. For the working-up, the solution was evaporated at 35° in vacuo, and the residue was chromatographed on 400 g of silica gel. Elution with hexane/ether (5:1) yielded 3.80 g of pure 4,5-dihydro-6'β-(hydroxymethyl)spiro[furan-2(3H),17'a(β1)-D-homoandrosta-4,16-dien]-3'-one which was dissolved in 250 ml of dioxan, treated within 10 minutes with 10 ml of 18% hydrochloric acid and subsequently stirred at room temperature for 1¾ hours. For the working-up, 18 g of sodium hydrogen carbonate were added thereto, the mixture was stirred at room temperature for 1 hour, the precipitate was filtered off, and the filtrate was concentrated in vacuo. There were obtained 3.5 g of beige crystals which were chromatographed on 150 g of silica gel. Pure 4,5-dihydro-6'-methylenespiro[furan-2(3H),17'a(β1)-D-homoandrosta-4,16-dien]-3'-one could be eluted with hexane/acetone (9:1). m.p. 167°–169°, $[\alpha]_D^{25} = +154.5°$ (c=0.6 in dioxane).

The starting material was prepared as follows:

5.0 g of 4,5-dihydrospiro[furan-2(3H),17'a(β1)-D-homoandrosta-4,16-dien]-3'-one was dissolved in 150 ml of methanol, treated with 3 ml of pyrrolidine and boiled under reflux for 5 minutes. The solution was then cooled to −15°. The precipitated enamine was filtered off under suction and dried at room temperature in vacuo. m.p. 176°–178°.

EXAMPLE A

| Lotion for topical use (e.g., in acne): | |
| --- | --- |
| Methyl 3-oxo-D-homo-androst-4-ene-17aβ-carboxylate | 2 g |
| 2-Phenylethyl alcohol | 15 ml |
| Glycerine | 5 ml |
| Ethanol q.s. | ad 100 ml |

EXAMPLE B

| Gel: | |
| --- | --- |
| 2-Diethylamino-ethyl 3-oxo-D-homo-androst-4-ene-17aβ-carboxamide hydrochloride | 5.00 g |
| Hydroxypropylcellulose | 2.60 g |
| Isopropanol | 30.00 g |
| Water | 0.10 g |
| Sodium ethylenediaminetetraacetate | 0.01 g |
| Propyleneglycol q.s. | ad 100.00 g |

EXAMPLE C

| Ointment: | |
| --- | --- |
| 2-Diethylamino-ethyl 3-oxo-D-homo-androst-4-ene-17aβ-carboxamide hydrochloride | 5 g |
| Wax (white) | 35 g |
| Lanolin alcohol | 5 g |
| Amerchol C | 15 g |
| Isopropyl myristate q.s. | ad 100 g |

What is claimed is:

1. D-homosteroids of the formula

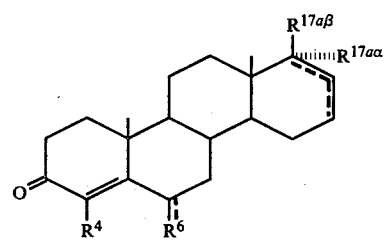

wherein $R^4$ is hydrogen, methyl, chlorine or hydroxy; $R^6$ is hydrogen or methylene; $R^{17a\alpha}$ is hydrogen, methyl or chlorine and $R^{17a\beta}$ is carboxy, esterified carboxy, cyano, formyl, carbamoyl, mono(lower alkyl)carbamoyl or di(lower alkyl)carbamoyl; or $R^{17a\alpha}$ and $R^{17a\beta}$ together are a spiroether ring of the formula

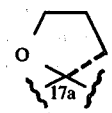

and wherein the dotted bonds in the D-ring are an optional 16(17)- or 17(17a)-double bond.

2. D-homosteroids in accordance with claim 1 wherein $R^4$, $R^6$ and $R^{17a\alpha}$ are hydrogen.

3. D-homosteroids in accordance with claim 1 wherein $R^{17a\beta}$ is carboxy, lower alkoxycarbonyl or cyano or $R^{17a\alpha}$ and $R^{17a\beta}$ together are a spiroether ring of the formula

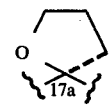

4. D-homosteroids in accordance with claim 1 wherein $R^4$, $R^6$ and $R^{17a\alpha}$ are hydrogen and $R^{17a\beta}$ is carboxy or lower alkoxycarbonyl and in which the D-ring is saturated.

5. The compound of claim 1 which is 3-oxo-D-homo-androst-4-ene-17aβ-carboxylic acid.

6. The compound of claim 1 which is methyl 3-oxo-D-homo-androst-4-ene-17aβ-carboxylate.

7. The compound of claim 1 which is isopropyl 3-oxo-D-homo-androsta-4,17-diene-17a-carboxylate.

8. The compound of claim 1 which is 2-diethylaminoethyl 3-oxo-D-homo-androsta-4,17-diene-17a-carboxylate.

9. The compound of claim 1 which is chloromethyl 3-oxo-D-homo-androsta-4,17-diene-17a-carboxylate.

10. The compound of claim 1 which is methyl 3-oxo-D-homo-androsta-4,17-diene 17a-carboxylate.

11. The compound of claim 1 which is methyl 17a-methyl-3-oxo-D-homo-androsta-4,16-diene-17aβ-carboxylate.

12. The compound of claim 1 which is 3-oxo-D-homo-androsta-4,17-diene-17a-carboxaldehyde.

13. The compound of claim 1 which is 3-oxo-D-homo-androsta-4,17-diene-17a-carboxylic acid.

14. The compound of claim 1 which is 4-methyl-3-oxo-D-homo-androsta-4,17-diene-17a-carboxylic acid.

15. The compound of claim 1 which is 4-methyl-3-oxo-D-homo-androst-4-ene-17aβ-carboxylic acid.

16. The compound of claim 1 which is methyl 3-oxo-4-methyl-D-homo-androst-4-ene-17aβ-carboxylate.

17. The compound of claim 1 which is methyl 4-chloro-3-oxo-D-homo-androsta-4,17-diene-17a-carboxylate.

18. The compound of claim 1 which is methyl 4-chloro-3-oxo-D-homo-androst-4-ene-17aβ-carboxylate.

19. The compound of claim 1 which is methyl 4-methyl-3-oxo-D-homo-androsta-4,17-diene-17a-carboxylate.

20. The compound of claim 1 which is methyl 17a-chloro-3-oxo-D-homo-androst-4-ene-17aβ-carboxylate.

21. The compound of claim 1 which is methyl 4-hydroxy-3-oxo-D-homo-androsta-4,17-diene-17a-carboxylate.

22. The compound of claim 1 which is methyl 4-hydroxy-3-oxo-D-homoandrost-4-ene-17aβ-carboxylate.

23. The compound of claim 1 which is 3-oxo-D-homo-androst-4-ene-17aβ-carboxaldehyde.

24. The compound of claim 1 which is 17a-methyl-3-oxo-D-homo-androsta-4,16-diene-17aβ-carboxylic acid.

25. The compound of claim 1 which is 3-oxo-D-homo-androst-4-ene-17aβ-carboxamide.

26. The compound of claim 1 which is dimethyl 3-oxo-D-homo-androst-4-ene-17aβ-carboxamide.

27. The compound of claim 1 which is methyl 3-oxo-D-homo-androsta-4,17-diene-17a-carboxamide.

28. The compound of claim 1 which is 2-diethylamino-ethyl 3-oxo-D-homo-androst-4-ene-17aβ-carboxamide hydrochloride.

29. The compound of claim 1 which is 3-oxo-D-homo-androst-4-ene-17aβ-carbonitrile.

30. The compound of claim 1 which is 4,5-dihydrospiro[furan-2(3H),17'a(β1)-D-homoandrosta-4,16-dien]-3'-one.

31. The compound of claim 1 which is 4,5-dihydro-6'-methylenespiro[furan-2(3H),17'a-(β1)-D-homoandrosta-4,16-dien]-3'-one.

32. A method for the treatment of acne and hirsutism which comprises administering to an organism suffering therefrom an effective amount of a D-homosteroid of claim 1.

33. A method for the treatment of prostate hypertrophy which comprises administering to an organism suffering therefrom an effective amount of a D-homosteroid of claim 1.

34. A pharmaceutical composition for the treatment of prostate hypertrophy which comprises effective amounts of a D-homosteroid derivative of claim 1 in combination with an inert carrier material.

* * * * *